(12) United States Patent
Pang et al.

(10) Patent No.: US 10,119,153 B2
(45) Date of Patent: Nov. 6, 2018

(54) **METHOD FOR ARACHIDONIC ACID PRODUCTION FROM *SALISPINA SPINOSA* (*HALOPHYTOPHTHORA SPINOSA*)**

(71) Applicant: National Taiwan Ocean University, Keelung (TW)

(72) Inventors: Ka-Lai Pang, Kaohsiung (TW); Han-Jia Lin, Kaohsiung (TW)

(73) Assignee: NATIONAL TAIWAN OCEAN UNIVERSITY, Keelung (TW)

( * ) Notice: Subject to any disclaimer, the term of this patent is extended or adjusted under 35 U.S.C. 154(b) by 248 days.

(21) Appl. No.: 14/582,313

(22) Filed: Dec. 24, 2014

(65) Prior Publication Data

US 2015/0184209 A1    Jul. 2, 2015

(30) Foreign Application Priority Data

Dec. 26, 2013   (TW) .............. 102148385 A

(51) Int. Cl.
*C12P 7/64*    (2006.01)
*C12N 1/14*    (2006.01)
*C12R 1/645*   (2006.01)

(52) U.S. Cl.
CPC .............. *C12P 7/6427* (2013.01); *C12N 1/14* (2013.01); *C12R 1/645* (2013.01)

(58) Field of Classification Search
None
See application file for complete search history.

(56) References Cited

PUBLICATIONS

Bajpai (Production of Docosahexaenoic Acid by Thraustochytrium aureum, 1991).*
Leano (Physiological Studies on Halophytophthora vesicula (Straminipilous Fungi) Isolated from Fallen Mangrove Leaves from Mai Po, Hong Kong, 1998).*

* cited by examiner

*Primary Examiner* — Scott Long
*Assistant Examiner* — Nghi V Nguyen
(74) *Attorney, Agent, or Firm* — Bacon & Thomas, PLLC

(57) ABSTRACT

The present invention provides a method for eicosapentaenoic acid (EPA) and/or arachidonic acid (ARA) production by using *Halophytophthora* and *Halophytophthora* isolates that are suitable for EPA and/or ARA production. The disclosure of the present invention provides another choice for the industry to produce EPA and ARA that are good for human's health and promotes the industrial value of *Halophytophthora*.

9 Claims, 2 Drawing Sheets
Specification includes a Sequence Listing.

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gtagtcatat gcttgtctc                                                  19

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
gcatcacaga cctgttattg cctc                                            24

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
tccgtaggtg aacctgcgg                                                  19

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tcctccgctt attgatatgc                                                 20

METHOD FOR ARACHIDONIC ACID PRODUCTION FROM *SALISPINA SPINOSA* (*HALOPHYTOPHTHORA SPINOSA*)

BACKGROUND

Technical Field

The present invention is related to a method for eicosapentaenoic acid and/or arachidonic acid production; more specifically, is related to a method for eicosapentaenoic acid and/or arachidonic acid production by *Halophytophthora*.

Description of Related Art

Polyunsaturated fatty acid (PUFA) is referred to as a group of fatty acids having at least one C=C double bonds in structure. The PUFA can be categorized into different subgroups, such as omega-3 (n-3) fatty acid, omega-6 (n-6) fatty acid, omega-9 (n-9) fatty acid, etc. The benefit of many common PUFA (ex. docosahexaenoic acid (DHA; 22:6 (n-3)), eicosapentaenoic acid (EPA; 20:5 (n-3)), and arachidonic acid (ARA; 20:4 (n-3))) to human health has been recognized. It is well-known that deep-sea fish has a lot of these PUFA, and mankind can intake these important nutrients by eating those fish. However, along with the increment of human population, the fish caught has been significantly decreased due to overfishing and the marine ecology is facing severe challenge. In this regard, the scientists in the field started to survey and study if we could obtain those beneficial PUFA from other organisms. In term of the advantage of ease to operate, microorganisms are the main target of the research; wherein, some micro-algae, fungi, and *Thraustochytrium* have been identified to have the value in eicosapentaenoic acid and arachidonic acid production.

*Halophytophthora* genus is a kind of heterotrophic microorganisms living at river mouth. *Halophytophthora* genus is one of the degraders of mangroves at its early living stage, and *Halophytophthora* can digest complex and big organic substances into smaller molecules, which is favorable to the nutrient cycling for the growth of mangroves. It is known that the *Halophytophthora* genus has 14 species: *Halophytophthora avicenniae*, *Halophytophthora bahamensis*, *Halophytophthora batemanensis*, *Halophytophthora elongate*, *Halophytophthora epistomia*, *Halophytophthora exoprolifera*, *Halophytophthora kandeliae*, *Halophytophthora masteri*, *Halophytophthora mycoparasitica*, *Halophytophthora operculata*, *Halophytophthora polymorphica*, *Halophytophthora porrigovesica*, *Salispina spinosa* (also known as *Halophytophthora spinosa* var. *spinosa*), *Halophytophthora spinosa* var *lobata*, and *Halophytophthora vesicula*; wherein, among them, *Halophytophthora vesicula* is the most common. Because *Halophytophthora* genus is close to *Pythium aphanidermatum* (which has been proved to be able to produce EPA and ARA) in evolution, the present research hypothesized the potential ability of *Halophytophthora* genus in EPA and ARA production and expected that the research results may provide another option for EPA and ARA production in the field.

SUMMARY

One of the objects of the present invention is to provide another option for EPA and ARA production so that the available sources of EPA and ARA, which is good for human health, can be increased and the acquisition cost can be decreased.

Another object of the present invention is to provide a method for producing EPA and ARA by using *Halophytophthora* so that the economic value of *Halophytophthora* can be improved.

In order to achieve the aforesaid objects, the present invention provides a method for eicosapentaenoic acid and/or arachidonic acid production, comprising isolating eicosapentaenoic acid and arachidonic acid from a *Halophytophthora*.

Preferably, said method further comprises a culture step before conducting said isolating; wherein said culture step comprises: culturing said *Halophytophthora* in a liquid medium for 4 to 10 days; wherein said medium is PYGS medium, Cornmeal medium, Potato Dextrose medium, or a combination thereof.

Preferably, said method further comprises a culture step before conducting said isolating; wherein said culture step comprises: culturing said *Halophytophthora* in a solid medium for 4 to 10 days to obtain a *Halophytophthora* colony; and culturing said colony in a liquid medium for 4 to 10 days; wherein said medium is PYGS medium, Cornmeal medium, Potato Dextrose medium, or a combination thereof.

Preferably, said medium comprises 1.0 to 3.5 wt % of salt; wherein said wt % is based on the total weight of said medium.

Preferably, said medium has a pH value of 5 to 9.

Preferably, said *Halophytophthora* is cultured at a temperature of 10 to 35° C.

Preferably, said PYGS medium comprises: 1 to 5 g/L of glucose; 1 to 5 g/L of yeast extract; 1 to 5 g/L of peptone; and 1 to 3.5% (v/v) of seawater; wherein said unit of concentration is based on the total volume of said PYGS medium.

Preferably, the yield of said eicosapentaenoic acid is 0 to 8 mg/L/day; wherein said day is calculated from the sum of the days that said *Halophytophthora* is cultured in said liquid medium.

Preferably, the yield of said arachidonic acid is 0.05 to 9 mg/L/day; wherein said day is calculated from the sum of the days that said *Halophytophthora* is cultured in said liquid medium.

Preferably, said *Halophytophthora* is *Halophytophthora avicenniae*, *Halophytophthora polymorphica*, *Halophytophthora spinosa*, *Halophytophthora vesicula*, or a combination thereof.

Preferably, said *Halophytophthora* is *Halophytophthora spinosa*, and said *Halophytophthora* culture substantially does not comprises eicosapentaenoic acid.

Preferably, said *Halophytophthora* has a deposition number of BCRC930163 at the Food Industry Research and Development Institute.

The present invention also provides a *Halophytophthora* capable of producing eicosapentaenoic acid and/or arachidonic acid, selecting from a group of *Halophytophthora* having a deposition number of BCRC930161, BCRC930162, and BCRC930163 at the Food Industry Research and Development Institute.

Preferably, said *Halophytophthora* is obtained by the following screening steps: (a) obtaining a mangrove leaf; (b) culturing said mangrove leaf in seawater to obtain a zoosporangium; (c) culturing said zoosporangium in a PYGS medium.

Preferably, said seawater of said step (b) is sterile seawater of a concentration of 2 to 3% (v/v).

Preferably, said PYGS medium comprises: 1 to 5 g/L of glucose; 1 to 5 g/L of yeast extract; 1 to 5 g/L of peptone;

and 1 to 3.5% (v/v) of seawater; wherein said unit of concentration is based on the total volume of said PYGS medium.

Preferably, said *Halophytophthora* has a deposition number of BCRC930163 at the Food Industry Research and Development Institute, and being not capable of producing eicosapentaenoic acid.

In light of the foregoing, the present invention proved the economic value of *Halophytophthora* in eicosapentaenoic acid and/or arachidonic acid production. Moreover, The BCRC930163 strain of *Halophytophthora* screened by the present invention shows specific ability in producing arachidonic acid but not eicosapentaenoic acid, which is useful in exclusive production of arachidonic acid.

BRIEF DESCRIPTION OF THE DRAWINGS

The indication of "a", "b", "c", "d", and "e" in FIG. 1 and FIG. 2 is marked for indicating the statistical significance between data. The statistical significance is calculated by the One-Way ANONA based on the Tukey Test. Data being identified as statistically significant through the aforesaid calculation are indicated with different English letters for distinction.

DETAILED DESCRIPTION

Figure 1:
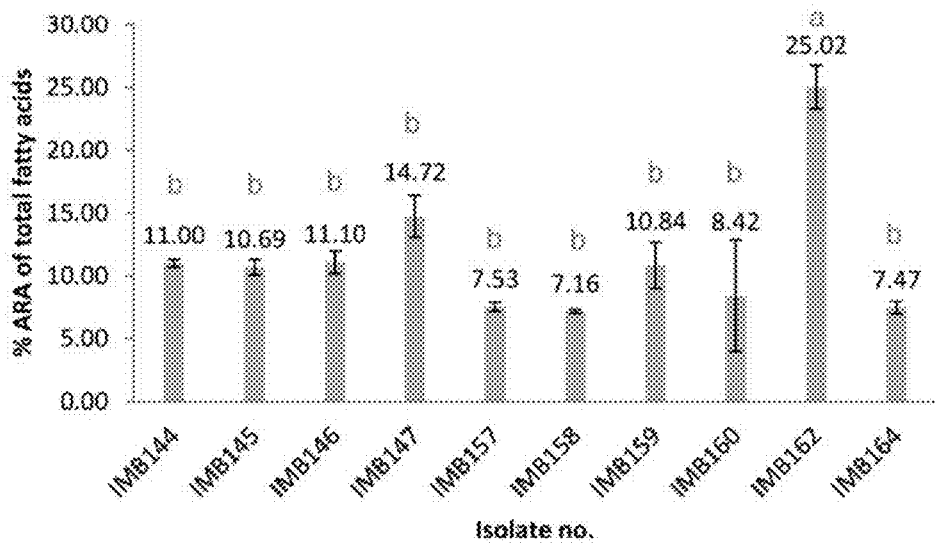
FIG. 1 shows the ARA production percentage of the isolated strains of the present invention.

The present invention provides a method for eicosapentaenoic acid and/or arachidonic acid production.

In one aspect of the present invention, said method comprises: isolating eicosapentaenoic acid and arachidonic acid from a *Halophytophthora*. Said *Halophytophthora* may be gathered from the field, may be sharing strains from research institutes, and may be commercial available strains. More specifically, said method is to isolate eicosapentaenoic acid and arachidonic acid from a group of *Halophytophthora*.

Alternatively, said method is to isolate eicosapentaenoic acid and arachidonic acid from a *Halophytophthora* culture. Said "*Halophytophthora* culture" comprises the body of *Halophytophthora* in the culture, culture medium, or a combination thereof. As *Halophytophthora* may change its morphology at different living stages thereof, said body preferably is referred to as mycelia.

In an embodiment of the present invention, said *Halophytophthora* is cultured by a culture step before said isolating. Said culture step comprises: culturing said *Halophytophthora* in a liquid medium for 4 to 10 days; wherein said medium is PYGS medium, Cornmeal medium, Potato Dextrose medium, or a combination thereof.

In another embodiment of the present invention, said *Halophytophthora* is cultured by a culture step before said isolating. Said culture step comprises: (A) an activation step; wherein said *Halophytophthora* is cultured in a solid medium for 4 to 10 days to obtain a *Halophytophthora* colony; and (B) a proliferation step; wherein said colony is cultured in a liquid medium for 4 to 10 days; wherein said solid medium and/or said liquid medium is PYGS medium, Cornmeal medium, Potato Dextrose medium, or a combination thereof. The days required for culturing can be varied according to the desired mass weight, the freshness of the culture medium, or the other factors.

Unless specifically indicated, said "medium" used herein comprises solid medium and/or liquid medium (culture solution). Said solid medium and/or liquid medium can be PYGS medium, Cornmeal medium, Potato Dextrose medium, or a combination thereof. Said PYGS medium comprises: 1 to 5 g/L of glucose; 1 to 5 g/L of yeast extract; 1 to 5 g/L of peptone; and 1 to 3.5% (v/v) of seawater (preferably, 2 to 3% (v/v) of seawater); wherein said unit of concentration is based on the total volume of said PYGS medium. In an alternative embodiment of the present invention, said solid medium also comprises 10 to 20 g/L of agar. In an alternative embodiment of the present invention, said solid medium and/or liquid medium may further comprise 0.1 to 1 g/L of antibiotic.

In a preferable embodiment of the present invention, said solid medium and/or liquid medium comprises 1.0 to 3.5 wt % of salt (based on the total weight of said medium), a pH value of 5 to 9, and said culture is conducted at 10 to 35° C. (preferably, 20 to 30° C.).

The method for isolating eicosapentaenoic acid and/or arachidonic acid from a *Halophytophthora* culture is not limited. Those having ordinary skill in the art can choice any isolation manner known in the art for this purpose; for instance, by using supercritical carbon dioxide extraction.

On the other hand, in an alternative embodiment of the present invention, said *Halophytophthora* is gathered from the field. The gather procedure is: (a) obtaining a mangrove leaf; the breed of the mangrove is not limited; for instance, the mangrove may be from Haomeili (Chiayi County, Taiwan), Shezi (Taipei City, Taiwan), Balli (Taipei City, Taiwan); (b) washing and cutting said mangrove leaf into pieces of proper size and culturing said mangrove leaf in seawater of suitable temperature to obtain a zoosporangium; said suitable temperature is at 20 to 30° C.; said seawater is at a concentration of 2 to 3% (v/v) and preferably is a sterile seawater that has been sterilized. (c) culturing said zoosporangium in a PYGS medium at 10 to 35° C.; said PYGS medium comprises 1 to 5 g/L of glucose; 1 to 5 g/L of yeast extract; 1 to 5 g/L of peptone; and 1 to 3.5% (v/v) of seawater; wherein said unit of concentration is based on the total volume of said PYGS medium; more preferably, said PYGS medium comprises 2 to 4 g/L of glucose; 2 to 4 g/L of yeast extract; 2 to 4 g/L of peptone; and 1.5 to 3.0% (v/v) of seawater.

In a preferable embodiment, the strain and method of present invention has an eicosapentaenoic acid yield of 0 to 8 mg/L/day; has an arachidonic acid yield of 0.05 to 9 mg/L/day; wherein said day is calculated from the sum of the days that said *Halophytophthora* is cultured in said liquid medium. In other words, the total production of eicosapentaenoic acid and arachidonic acid is increasing over the culture time.

The following embodiments are recited for more clearly explaining the researches and advantages of the present invention. It is important to note that the following embodiments are only exemplary for the aforesaid purposes and shall not limit the claimed scope of the present invention.

Example 1: The Gathering and Identification of the Present *Halophytophthora*

This example recorded the gathering and identification of the present *Halophytophthora*.

Yellowish green mangrove leaves were gathered (from Haomeili, Chiayi County, Taiwan; Shezi, Taipei City, Taiwan; or Bali, Taipei City, Taiwan) and maintained in cold box for delivering to the lab (National Taiwan Ocean University, Keelung, Taiwan). The impurity on the leaves was washed off by water and then the leaves were soaked in sterile seawater (2.5% (v/v)). The leaves were then cut into 1 cm$^2$ and inoculated in sterile seawater (2.5% (v/v)) at room temperature for zoosporangium production. After that, the zoosporangium was picked and inoculated on PYGS solid medium (4 g/L of glucose; 4 g/L yeast extract; 4 g/L peptone; 12 g/L agar; 2.5% (v/v) of seawater; 0.5 g/L of penicillin G sodium salt; and 0.5 g/L of streptomycin sulfate) at 25° C. A total of 10 strains were obtained in this example and they were identified through morphology recognition and 18S/ITS analysis.

For morphology recognition, those strain were cultured respectively in VF9 medium (containing 50% of commercially-available nutrition; Evergreen 579, 0.3% of $Na_2CO_3$, 12 g/L of agar, and 2.5% (v/v) of seawater) for a week. The colonies were dug out and inoculated in sterile seawater (2.5% (v/v)) to induce sporulation. Lastly, the morphology of the zoosporangium of the stain was identified according to the finding of Nakagiri (2002).

For molecular analysis, the mycelium was scraped from the PYGS solid medium and ground in liquid nitrogen by using a mortar. Then, the genome DNA was extracted by using DNeasy Plant DNA Extraction kit (Qiagen) and the nuclear rRNA was amplified by polymerase chain reaction (PCR) with the primer sets listed in the following table 2. PCR reactions were performed in a 25 µL volume containing 20 ng DNA, 0.2 µM of each primer, 0.2 mM of dNTP, 2.5 mM $MgCl_2$ and 1.25 U of Taq Polymerase (Invitrogen). The amplification cycle consisted of an initial denaturation step of 95° C. for 2 min followed by 35 cycles of (a) denaturation (95° C. for 1 min), (b) annealing (54° C. for 1 min) and (c) elongation (72° C. for 1.5 min) and a final 10 min elongation step at 72° C.

The obtained PCR products were sequenced and aligned with the NCBI database. The 10 strains were confirmed as listed in the table 1. The strains numbered IMB146, IMB157, IMB162 were deposited at the Food Industry Research and Development Institute and being allocated the deposition number of BCRC930161, BCRC930162, and BCRC930163, respectively.

Specifically, the microorganism BCRC930163 (IMB162) was deposited on Apr. 16, 2018, at the Leibniz Institute DSMZ—German Collection of Microorganisms and Cell Cultures (DSMZ), Inhoffenstr. 7B, D-38124 Braunschweig, Germany. The deposited microorganism was given the accession number DSM 32804.

TABLE 1

The 10 isolated *Halophytophthora* strains of the present invention

| Taxa | Isolate number | Substrates | Locality |
| --- | --- | --- | --- |
| *Halophytophthora avicenniae* | IMB144 | Fallen mangrove leaf | Haomeili, Chiayi County, Taiwan |
| *Halophytophthora avicenniae* | IMB145 | Fallen mangrove leaf | Haomeili, Chiayi County, Taiwan |
| *Halophytophthora polymorphica* | IMB146 | Fallen mangrove leaf | Haomeili, Chiayi County, Taiwan |
| *Halophytophthora vesicula* | IMB147 | Fallen mangrove leaf | Haomeili, Chiayi County, Taiwan |
| *Halophytophthora avicenniae* | IMB157 | Fallen mangrove leaf | Shezi, Taipei City, Taiwan |
| *Halophytophthora* sp. | IMB158 | Fallen mangrove leaf | Shezi, Taipei City, Taiwan |

TABLE 1-continued

The 10 isolated *Halophytophthora* strains of the present invention

| Taxa | Isolate number | Substrates | Locality |
| --- | --- | --- | --- |
| *Halophytophthora avicenniae* | IMB159 | Fallen mangrove leaf | Shezi, Taipei City, Taiwan |
| *Halophytophthora avicenniae* | IMB160 | Fallen mangrove leaf | Shezi, Taipei City, Taiwan |
| *Salispina spinosa* | IMB162 | Fallen mangrove leaf | Bali, Taipei City, Taiwan |
| *Halophytophthora* sp. | IMB164 | Fallen mangrove leaf | Bali, Taipei City, Taiwan |

TABLE 2

Primer sets used for molecular analysis

| Name | Sequence | Target |
| --- | --- | --- |
| NS1 SEQ ID NO 1 | 5'-GTAGTCATATGCTTGTCTC-3' | 18S rRNA |
| NS6 SEQ ID NO 2 | 5'-GCATCACAGACCTGTTATTGCCTC-3' | 18S rRNA |
| ITS1 SEQ ID NO 3 | 5'-TCCGTAGGTGAACCTGCGG-3' | ITS |
| ITS4 SEQ ID NO 4 | 5'-TCCTCCGCTTATTGATATGC-3' | ITS |

Example 2: Culturing the Present *Halophytophthora* and Analyzing the Contained Eicosapentaenoic Acid and/or Arachidonic Acid The isolated strain was cultured respectively in PYGS solid medium (4 g/L of glucose; 4 g/L yeast extract; 4 g/L peptone; 12 g/L agar; 2.5% (v/v) of seawater; 0.5 g/L of penicillin G sodium salt; and 0.5 g/L of streptomycin sulfate; the salt content is 2.5 wt %; 25° C.; pH=6.75) for one week. Then, the cultured mycelium was put into PYGS liquid medium (4 g/L of glucose; 4 g/L yeast extract; 4 g/L peptone; 2.5% (v/v) of seawater; 0.5 g/L of penicillin G sodium salt; and 0.5 g/L of streptomycin sulfate; the salt content is 2.5 wt %; 25° C.; pH=6.75) for another one week. After that, the cultured mycelium masses were transferred to Eppendorf tubes and spun down by centrifugation at 16,249 g, 25° C. for 10 minutes. The supernatant was removed and the mycelial masses were washed with sterile distilled water and pelleted down by centrifugation for 10 minutes with the supernatant removed. After repeating the washing and centrifugation several times as required, the tubes were then frozen at −80° C. overnight and freeze-dried for use in the successive fatty acid composition analysis.

In order to be used in the fatty acid composition analysis, 30 mg of each sample was obtained and mixed with 75 µL of chloroform containing 1 mg C19:0 fatty acid as an internal standard (Sigma-Aldrich, St. Louis, Mo., USA) and exhaustively extracted with 5 mL chloroform/methanol (2:1, v/v).

Then, a saponification/esterification reaction was conducted. The samples were each mixed with 2 mL 0.5 N NaOH methanol solution, heated in a 90° C. water bath for 15 min, cooled to room temperature. The sample was mixed with 2 mL of 0.7N HCl/methanol solution and 1 mL of 14% boron trifluoride/methanol solution (Sigma-Aldrich, St. Louis, Mo., USA) and again heated in 90° C. water bath for 15 minutes, and then cooled again. Next, 3 mL of saturated NaCl solution and 2 mL of n-hexane were added and mixed. The upper layer of water-phase content was transferred into a 4 mL amber vial and dried with a nitrogen stream. The opening of the vial was sealed by Parafilm® and the vial was stored at −20° C. until analysis could be performed.

Figure 2:
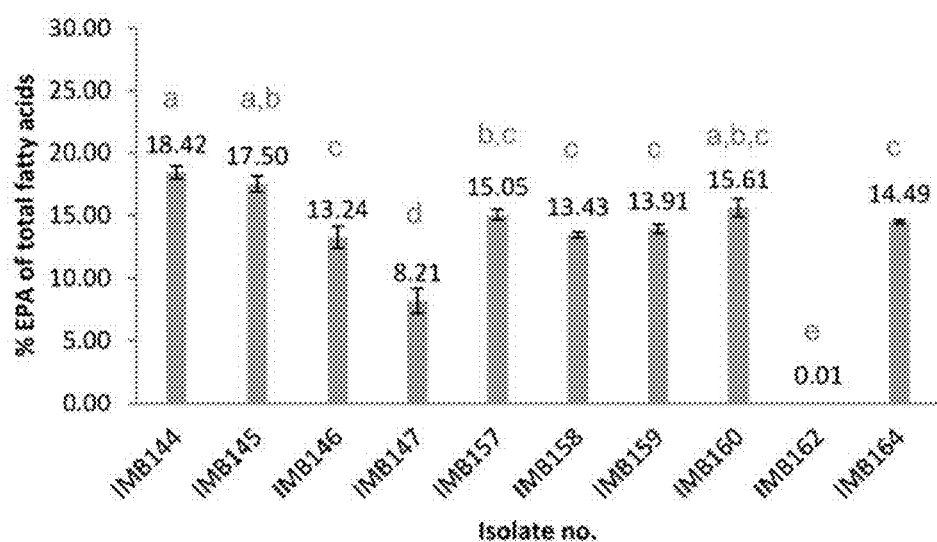
FIG. 2 shows the EPA production percentage of the isolated strains of the present invention.

A CP-380 gas chromatography machine equipped with a 320 single-quadrupole mass spectrometer (Varian, Palo Alto, Calif., USA) and a Supelco SP-2380 capillary column (30 m×0.25 mm i.d.; Sigma-Aldrich, St. Louis, Mo., USA) was used for analyzing the fatty acid methyl ester sample (FAME). The temperature of the injector and interface were set at 250° C. and 270° C., respectively. Also, the temperature of the column was set to rise from 50° C. to 150° C. with a heating rate of 15° C./min and then raise from 150° C. to 250° C. with a heating rate of 3° C./min. The linear velocity of the carrier gas was 38.0 cm/min. Methyl esters prepared from fatty acids including C20:2n-6, C20:4n-6, C22:2n-6, C22:3n-3, and C22:5n-6, and an FAME standard mixture (Supelco 18919-1AMP) were all purchased from Sigma-Aldrich and used as standards for identifying fatty acids in the samples. The fatty acids examined in each sample were quantified based on their peak area relative to the C19:0 fatty acid internal standard and displayed as a percentage of the total fatty acid content. The experimental results are shown in FIG. 1, FIG. 2 and table 3.

TABLE 3 the yield of ARA and EPR of the isolated strains of the present invention after culturing for one week

| Classification | Isolate number | Mass Weight (g/L) | Yield (g/L) | |
|---|---|---|---|---|
| | | | ARA | EPA |
| Halophytophthora avicenniae | IMB144 | 1.647 | 0.022 | 0.037 |
| Halophytophthora avicenniae | IMB145 | 1.710 | 0.020 | 0.034 |
| Halophytophthora polymorphica | IMB146 | 1.807 | 0.022 | 0.026 |
| Halophytophthora vesicula | IMB147 | 1.017 | 0.004 | 0.002 |
| Halophytophthora avicenniae | IMB157 | 2.510 | 0.023 | 0.047 |
| Halophytophthora sp. | IMB158 | 1.093 | 0.008 | 0.015 |
| Halophytophthora avicenniae | IMB159 | 2.173 | 0.019 | 0.025 |
| Halophytophthora avicenniae | IMB160 | 2.133 | 0.011 | 0.023 |
| Halophytophthora spinosa var spinosa | IMB162 | 2.333 | 0.052 | 0.000 |
| Halophytophthora sp. | IMB164 | 0.707 | 0.007 | 0.013 |

The culturing days of the experiment conducted in this example are 7 days. According to table 3, the average mass weight of the 10 isolated strains after 7 days culture is from 0.707 g/L to 2.510 g/L. IMB157 strain exhibited the fastest growth rate and the most average mass weight. Besides, IMB157 strain had the highest EPA yield among the others. On the other hand, IMB162 strain had the highest yield of ARA. To sum up, the average yield of ARA of the present 10 Halophytophthora isolated strains is from 0.54 to 7.41 mg/L/day, and the average yield of EPA is from 0 to 6.64 mg/L/day. In light of the experimental data, although the ARA or EPA yield of Halophytophthora is not always higher than other microorganisms conventionally used for PUFA production, Halophytophthora is particularly suitable for ARA and EPA production as most of the present isolated strain produce the two valuable PUFA at a percentage of about 10%. The information provides the field a novel option of PUFA production.

It is also important to note that the IMB162 strain of the present invention substantially did not produce EPA and the production of ARA constituted a quarter of the total fatty acid production. This means that the IMB162 strain can be particularly used for ARA production. In this way, the ARA purification steps in the production process can be reduced and it shall be extremely favorable for mass production of commercial scale.

Example 3: The Optimum Condition of the Present *Halophytophthora*

According to the experimental results of Example 2, the two isolated strains have the highest EPA and ARA yield respectively are IMB157 strain and IMB162 strain. The two strains were exactly two strains having the fastest growth rate (the one-week mass weight is 2.510 g/L and 2.333 g/L, respectively). Moreover, the correlation coefficient between EPA/ARA yield and mass weight is 0.77 (deducting IMB162, which does not produce EPA) and 0.67. It is appreciated that if an optimum condition for *Halophytophthora* growth can be developed, then the optimum condition for EPA and/or ARA production can be also obtained.

The salt content, pH value, and temperature of *Halophytophthora* culture were adjusted in this example as variable factors. In other words, the present 10 isolated strains were cultured in accordance with the culture steps set forth in the Example 2 but the salt content, pH value, and temperature in the culture were varied to try out an optimum condition that provides the best growth quality for said isolated strains.

Figure 3:
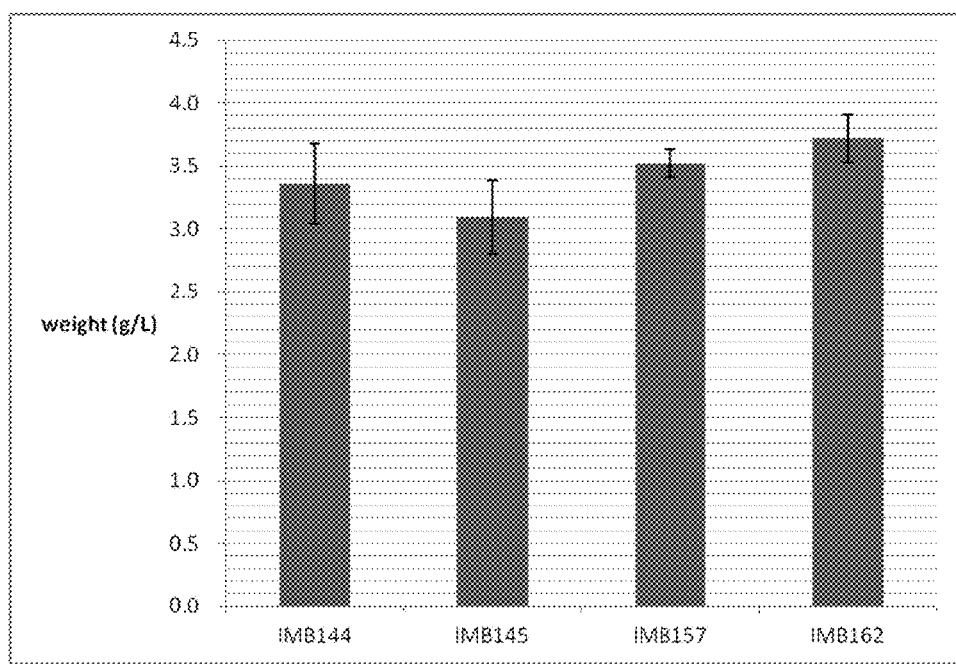
FIG. 3 shows the average mass weight of the present IMB144, IMB145, IMB157, and IMB162 strains respectively under optimum condition of the present invention.

According to the trials, the optimum condition of the present IMB144, IMB145, IMB157, and IMB162 strains were listed in the following table 4 and FIG. 3 (the additional data for the other isolated strains were not shown in this specification).

TABLE 4

The optimum condition of the IMB144, IMB145, IMB157, and IMB162 strains

| No. | Mass Weight (g/L) | | | Average Mass Weight(g/L) | Optimum Condition |
|---|---|---|---|---|---|
| IMB144 | 3.216 | 3.144 | 3.728 | 3.363 | Salt content: 1.5 wt %, 15° C., pH 7 |
| IMB145 | 2.786 | 3.372 | 3.126 | 3.095 | Salt content: 2 wt %, 25° C., pH 6 |
| IMB157 | 3.404 | 3.616 | 3.548 | 3.523 | Salt content: 3 wt %, 20° C., pH 5 |
| IMB162 | 3.820 | 3.840 | 3.500 | 3.720 | Salt content: 1.5 wt %, 25° C., pH 6 |

It was noted from the trial results that the optimum condition for *Halophytophthora* to grow and produce EPA and/or ARA was 1.0 to 3.0 weight percentage of salt content, pH 5 to 8, and 10 to 30° C. Under this condition, the growth rate of each isolated strain was stable, the growth quality is good and the diversity between each isolated strain is not significant. In other word, the condition shall be suitable for all *Halophytophthora* in mass production of commercial scale.

What is claimed is:

1. A method for arachidonic acid production, comprising isolating arachidonic acid from a *Salispina spinosa* strain,
    wherein said *Salispina spinosa* strain has a deposition number of DSM 32804 at the Leibniz Institute DSMZ—German Collection of Microorganisms and Cell Cultures.

2. The method of claim 1, further comprising a culture step before conducting said isolating; wherein said culture step comprises:
    culturing said *Salispina spinosa* strain in a liquid medium for 4 to 10 days; wherein said medium is PYGS medium, Cornmeal medium, Potato Dextrose medium, or a combination thereof.

3. The method of claim 1, further comprising a culture step before conducting said isolating; wherein said culture step comprises:
    culturing said *Salispina spinosa* strain in a solid medium for 4 to 10 days to obtain a *Salispina spinosa* strain colony; and
    culturing said colony in a liquid medium for 4 to 10 days; wherein said medium is PYGS medium, Cornmeal medium, Potato Dextrose medium, or a combination thereof.

4. The method of claim 3, wherein said medium comprises 1.0 to 3.5 wt % of salt; wherein said wt % is based on the total weight of said medium.

5. The method of claim 3, wherein said medium has a pH value of 5 to 9.

6. The method of claim 3, wherein said *Salispina spinosa* strain is cultured at a temperature of 10 to 35° C.

7. The method of claim 3, wherein said PYGS medium comprises:
    1 to 5 g/L of glucose;
    1 to 5 g/L of yeast extract;
    1 to 5 g/L of peptone; and
    1 to 3.5% (v/v) of seawater;
    Wherein said unit of concentration is based on the total volume of said PYGS medium.

8. The method of claim 3, wherein the yield of said arachidonic acid is 0.05 to 9 mg/L/day; wherein said day is calculated from the sum of the days that said *Salispina spinosa* strain is cultured in said liquid medium.

9. The method of claim 7, wherein said PYGS medium comprises:
   1 to 5 g/L of glucose;
   1 to 5 g/L of yeast extract;
   1 to 5 g/L of peptone; and
   2 to 3% (v/v) of seawater;
wherein said unit of concentration is based on the total volume of said PYGS medium.

* * * * *